US010524518B1

(12) United States Patent
Tygett

(10) Patent No.: US 10,524,518 B1
(45) Date of Patent: Jan. 7, 2020

(54) DUAL COIL VAPORIZER INHALATION CARTRIDGE FOR HIGH VISCOSITY OIL OR RESIN

(71) Applicant: Brett William Tygett, Folsom, CA (US)

(72) Inventor: Brett William Tygett, Folsom, CA (US)

( * ) Notice: Subject to any disclaimer, the term of this patent is extended or adjusted under 35 U.S.C. 154(b) by 0 days.

(21) Appl. No.: 16/589,388

(22) Filed: Oct. 1, 2019

Related U.S. Application Data

(63) Continuation-in-part of application No. 15/713,701, filed on Sep. 25, 2017.

(51) Int. Cl.
*A24F 47/00* (2006.01)
*A61M 11/04* (2006.01)

(52) U.S. Cl.
CPC .......... *A24F 47/008* (2013.01); *A61M 11/042* (2014.02); *A61M 2205/8206* (2013.01)

(58) Field of Classification Search
CPC ...... A24F 47/00; A24F 47/002; A24F 47/008; A61M 11/042; A61M 15/06; A61M 2205/8206
See application file for complete search history.

(56) References Cited

U.S. PATENT DOCUMENTS

| | | | | |
|---|---|---|---|---|
| 2015/0320116 A1* | 11/2015 | Bleloch | ............... | A61M 15/06 219/628 |
| 2016/0219937 A1* | 8/2016 | Rado | ..................... | A24F 47/008 |
| 2016/0360790 A1* | 12/2016 | Calfee | ............... | A61M 5/31548 |
| 2017/0027223 A1* | 2/2017 | Eksouzian | ............. | A24F 47/008 |
| 2018/0263283 A1* | 9/2018 | Popplewell | .......... | G05B 13/024 |
| 2019/0014822 A1* | 1/2019 | Bless | .................... | A24F 47/008 |
| 2019/0022345 A1* | 1/2019 | Kotch | ................. | A61M 16/145 |
| 2019/0037928 A1* | 2/2019 | Fornarelli | ............. | A24F 47/008 |
| 2019/0091423 A1* | 3/2019 | Tygett | .................. | A61M 15/06 |

* cited by examiner

*Primary Examiner* — Kristen Matter
(74) *Attorney, Agent, or Firm* — Craig A. Simmermon

(57) ABSTRACT

Dual coil vaporizer inhalation cartridge for high viscosity oil or resin is a specially designed vapor cartridge that includes a second independent heating coil in the oil tank or tank chamber that heats the inhalation oil or resin to reduce its viscosity prior to entering the vaporization chamber where it is vaporized for inhalation. Dual coil vaporizer inhalation cartridge for high viscosity oil or resin uses special electronics to power and control the tank heating coil with the battery and battery switch on a standard battery module for a vaporizer inhalation device, which also powers and controls the vaporization heating coil. The tank heating coil functions to heat and melt the oil/resin or otherwise lower its viscosity to allow the oil/resin to become more thin and runny so that the material may flow more easily through the wick and its capillary action to be successfully transferred to the atomizer heating coil for vaporization.

3 Claims, 11 Drawing Sheets

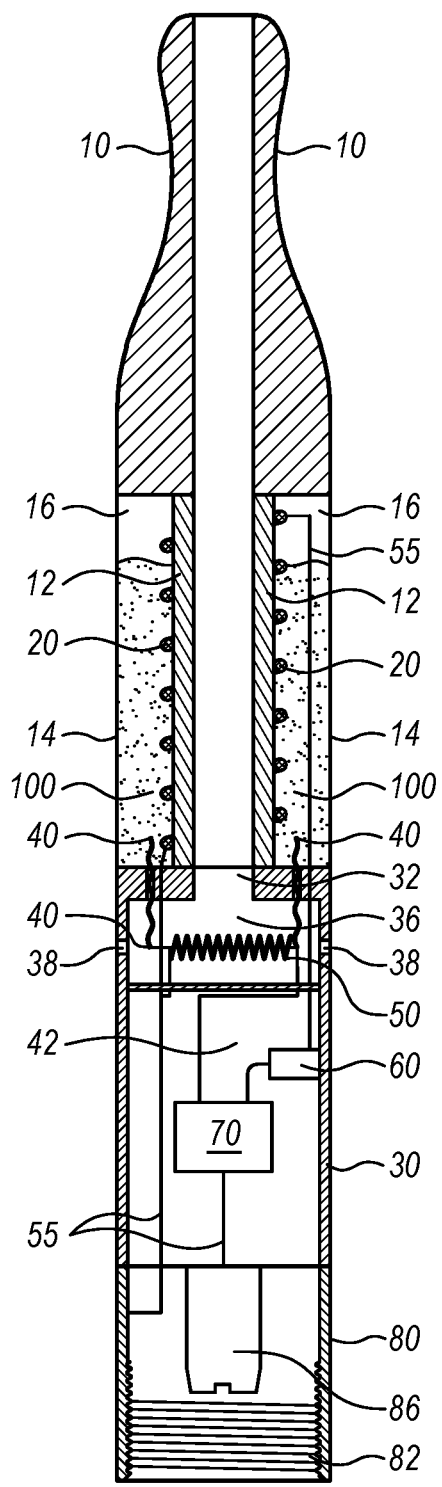
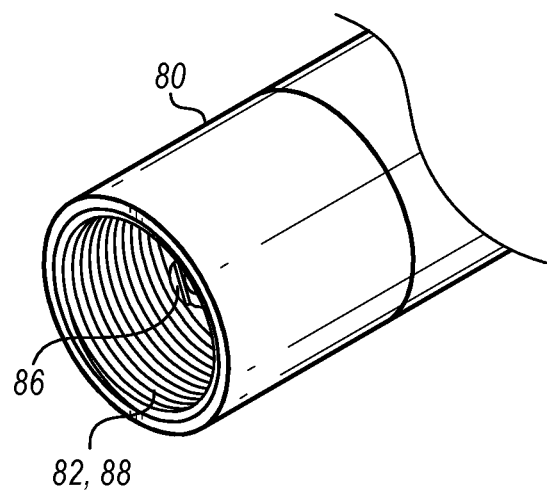
FIG. 8A
FIG. 8

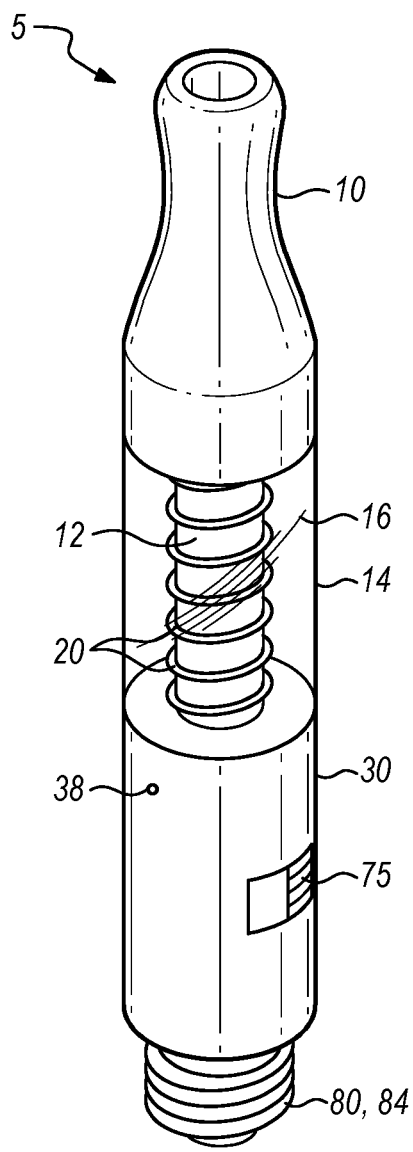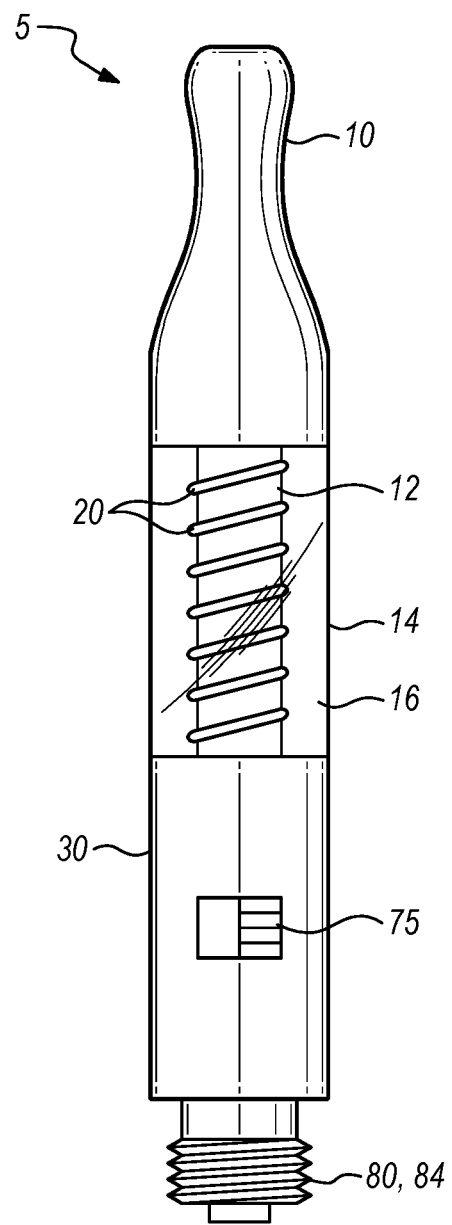
FIG. 9
FIG. 10

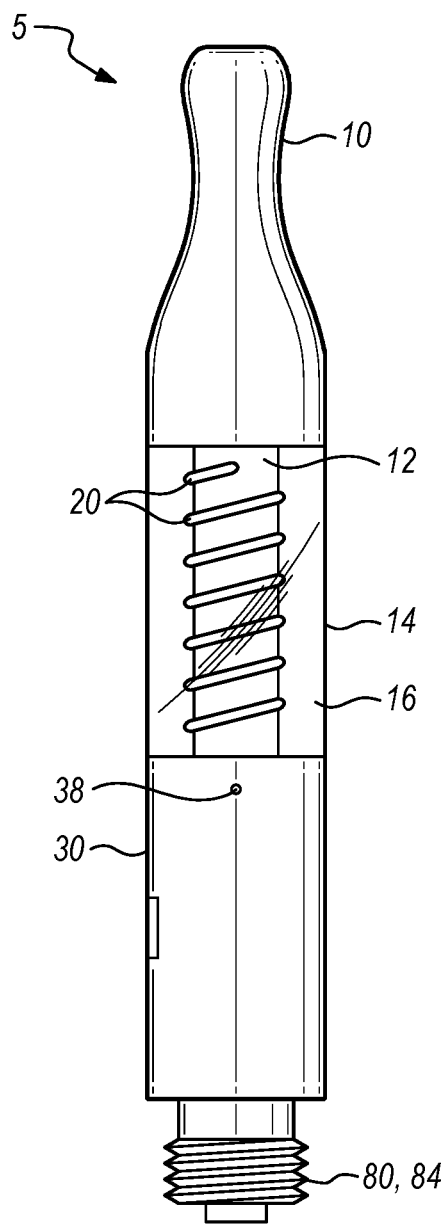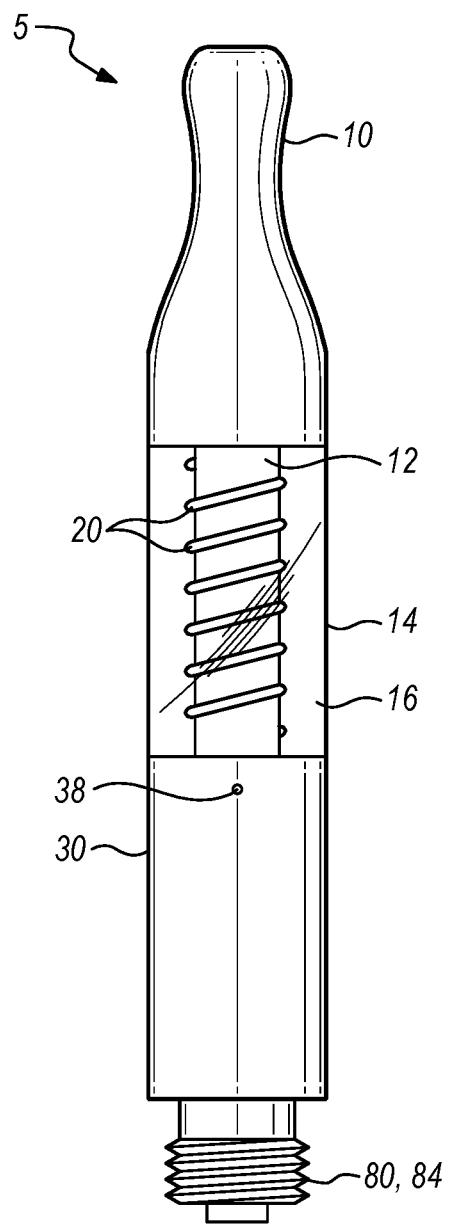
*FIG. 11*      *FIG. 12*

DUAL COIL VAPORIZER INHALATION CARTRIDGE FOR HIGH VISCOSITY OIL OR RESIN

CROSS-REFERENCE TO RELATED APPLICATIONS

The instant application is a continuation-in-part of U.S. application Ser. No. 15/713,701 entitled "Hot Oil Tank" filed on Sep. 25, 2017, which is hereby incorporated by reference herein.

BACKGROUND OF THE INVENTION

1. Field of the Invention

This invention is related to a vaporizer inhalation cartridge. The vaporizer inhalation cartridge of this invention is specially designed to include a second independent heating coil in the oil tank or tank chamber that heats the inhalation oil to reduce its viscosity prior to entering the vaporization chamber where it is vaporized for inhalation. This tank heating coil allows this vaporizer inhalation cartridge to process extremely high viscosity oils such as resin or tar-like substances. A special electronics design is included to power and control the tank heating coil as well as the atomizer heating coil with any standard battery module.

2. Description of Related Art

There are many vaporizer inhalation cartridges in the prior art however there are none with a tank heating coil and an atomizer heating coil. Also, there are no vaporizer inhalation cartridges with two heating coils that are both powered by a single battery and controlled with a single switch.

BRIEF SUMMARY OF THE INVENTION

It is an aspect of dual coil vaporizer inhalation cartridge for high viscosity oil or resin to include two independent heating coils: one heating coil in the tank chamber and one heating coil in the vaporization chamber.

It is an aspect of dual coil vaporizer inhalation cartridge for high viscosity oil to power both heating coils with one battery.

It is an aspect of dual coil vaporizer inhalation cartridge for high viscosity oil to control both heating coils with one battery switch.

It is an aspect of dual coil vaporizer inhalation cartridge for high viscosity oil to control both heating coils with a single pole double throw switch.

It is an aspect of dual coil vaporizer inhalation cartridge for high viscosity oil to power the tank chamber heating coil with a voltage regulator.

It is an aspect of tank chamber heating coil to heat up to melt or reduce the viscosity of high viscosity essential oil or resin stored in the tank chamber of dual coil vaporizer inhalation cartridge for high viscosity oil or resin in order to allow the wick to more easily absorb the melted material.

It is an aspect of dual coil vaporizer inhalation cartridge for high viscosity oil or resin to process highly viscous materials for successful vaporization and inhalation by the user.

It is an aspect of dual coil vaporizer inhalation cartridge for high viscosity oil or resin to include a mode with male thread on the proximal end that is capable of engagement with a female thread on a battery module.

It is an aspect of dual coil vaporizer inhalation cartridge for high viscosity oil or resin to include a mode with female thread on the proximal end that is capable of engagement with a male thread on a battery module.

BRIEF DESCRIPTION OF THE DRAWINGS

FIG. 8 is a longitudinal cross sectional view of first embodiment dual coil vaporizer inhalation cartridge for high viscosity oil or resin.

FIG. 8A is an enlarged view of the distal end of first embodiment dual coil vaporizer inhalation cartridge for high viscosity oil or resin.

FIG. 9 is a perspective view of a second embodiment of dual coil vaporizer inhalation cartridge for high viscosity oil or resin.

FIG. 10 is a front elevation view of second embodiment dual coil vaporizer inhalation cartridge for high viscosity oil or resin.

FIG. 11 is a left side elevation view of second embodiment dual coil vaporizer inhalation cartridge for high viscosity oil or resin, where the right side elevation view is a mirror image thereof.

FIG. 12 is a rear side elevation view of second embodiment dual coil vaporizer inhalation cartridge for high viscosity oil or resin.

DEFINITION LIST

Figure 1:
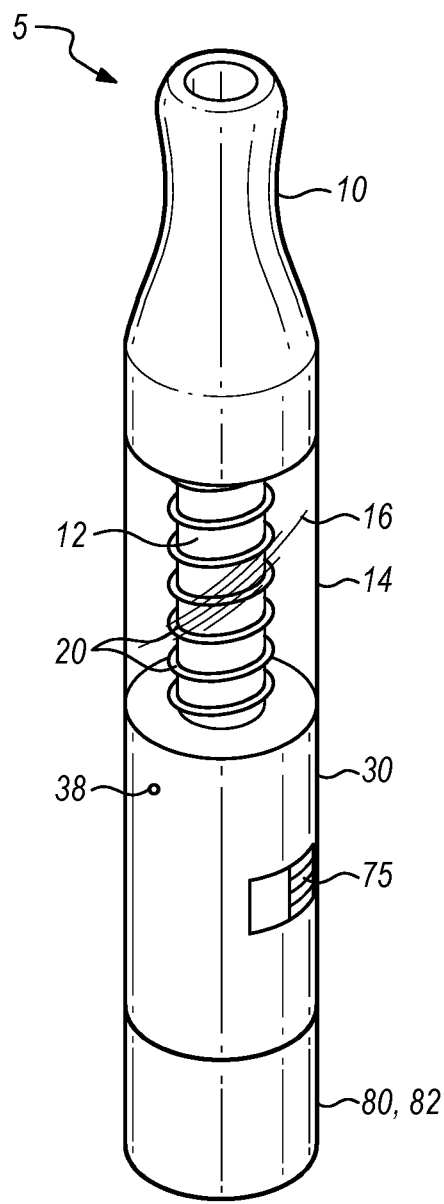
FIG. 1 is a perspective view of a first embodiment of dual coil vaporizer inhalation cartridge for high viscosity oil or resin.
Figure 2:
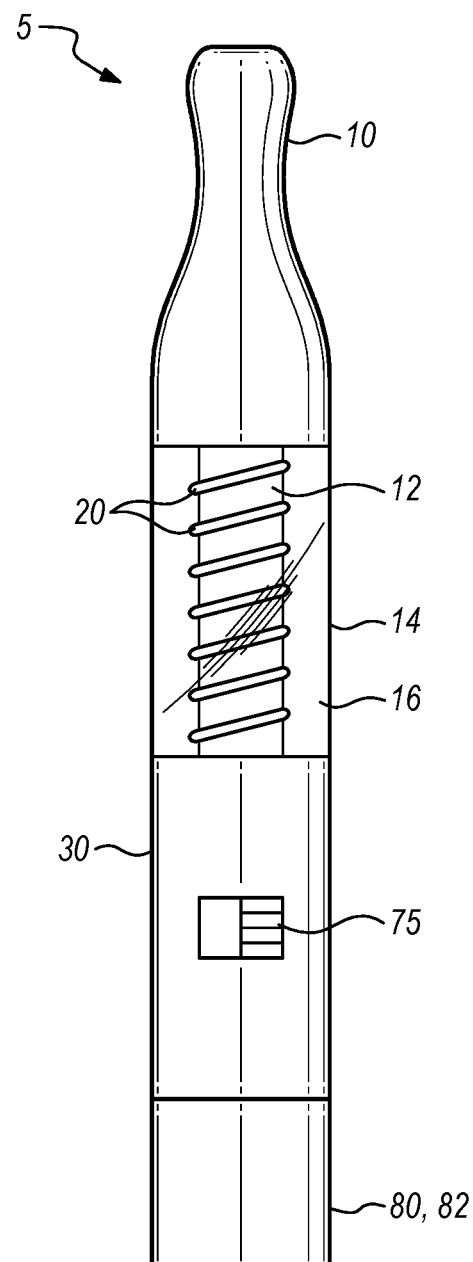
FIG. 2 is a front elevation view of first embodiment dual coil vaporizer inhalation cartridge for high viscosity oil or resin.
Figure 3:
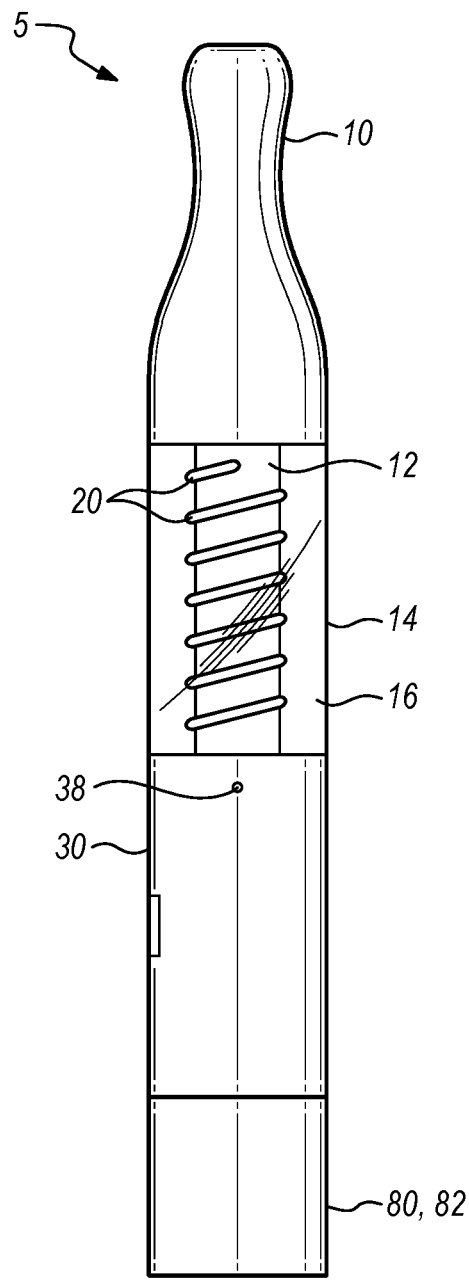
FIG. 3 is a left side elevation view of first embodiment dual coil vaporizer inhalation cartridge for high viscosity oil or resin, where the right side elevation view is a mirror image thereof.
Figure 4:
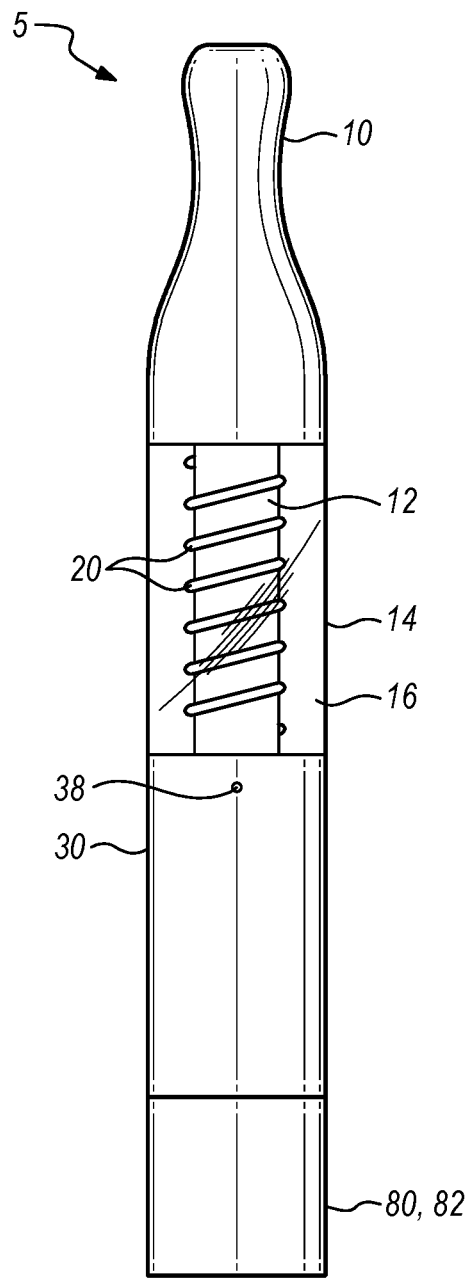
FIG. 4 is a rear side elevation view of first embodiment dual coil vaporizer inhalation cartridge for high viscosity oil or resin.
Figure 5:
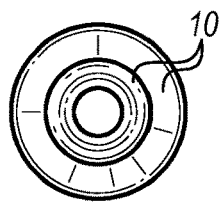
FIG. 5 is a top plan view of first embodiment dual coil vaporizer inhalation cartridge for high viscosity oil or resin.
Figure 6:
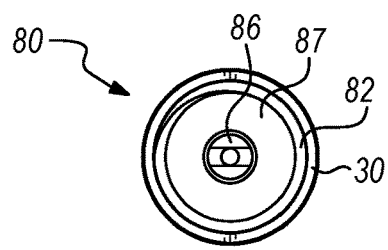
FIG. 6 is a bottom plan view of first embodiment dual coil vaporizer inhalation cartridge for high viscosity oil or resin.
Figure 7:
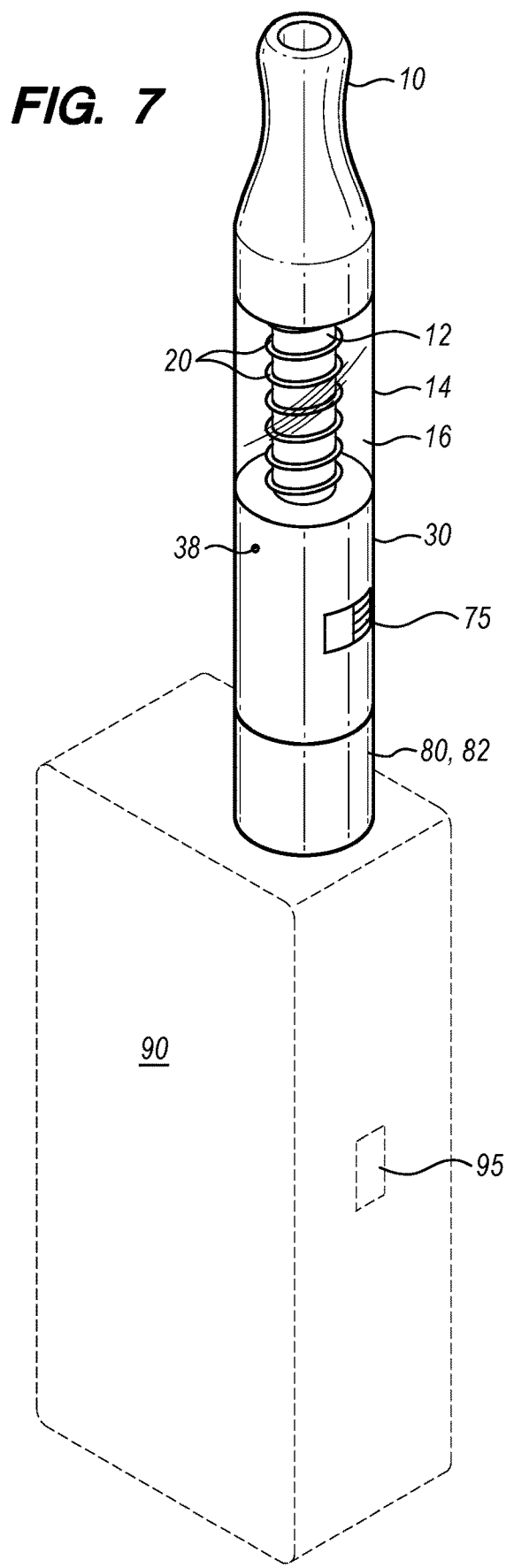
FIG. 7 is an environmental view of first embodiment dual coil vaporizer inhalation cartridge for high viscosity oil or resin attached to a battery module.
Figure 13:
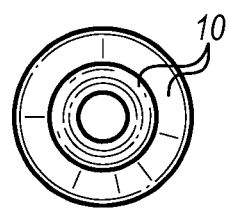
FIG. 13 is a top plan view of second embodiment dual coil vaporizer inhalation cartridge for high viscosity oil or resin.
Figure 14:
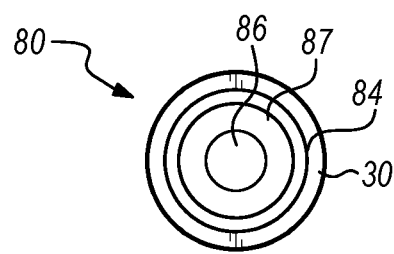
FIG. 14 is a bottom plan view of second embodiment dual coil vaporizer inhalation cartridge for high viscosity oil or resin.
Figure 15:
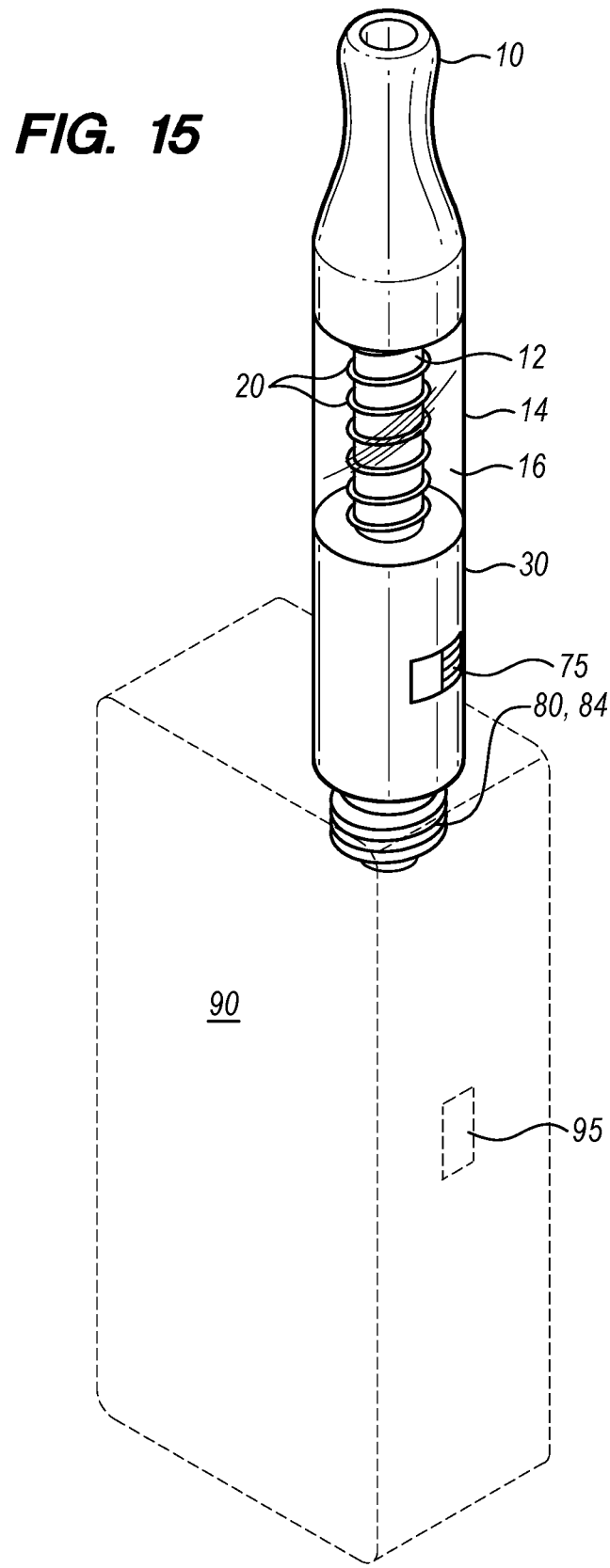
FIG. 15 is an environmental view of second embodiment dual coil vaporizer inhalation cartridge for high viscosity oil or resin attached to a battery module.
Figure 16:
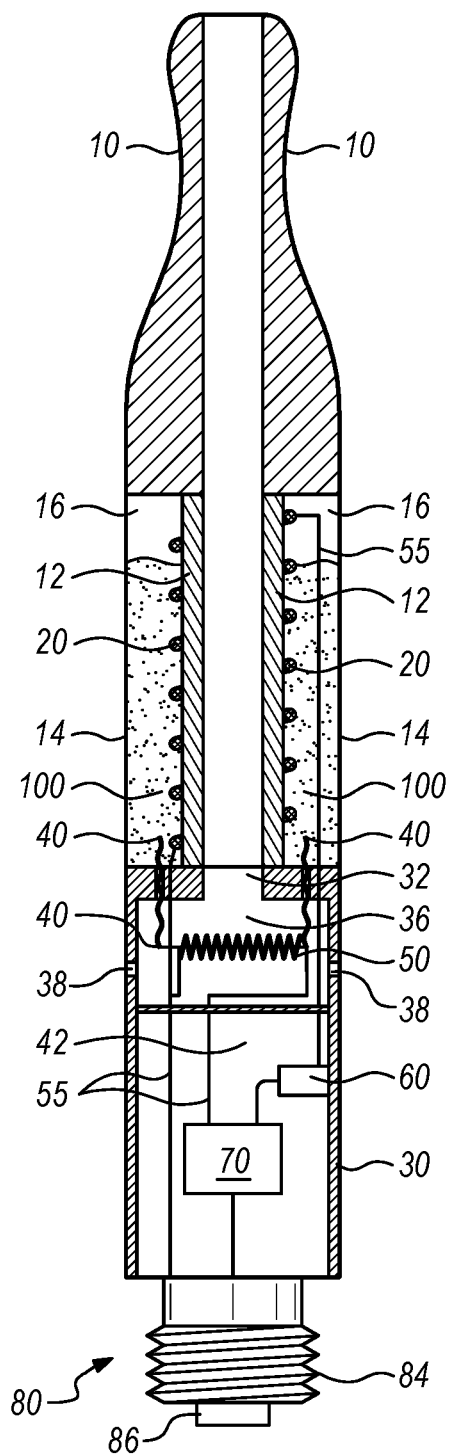
FIG. 16 is a longitudinal cross sectional view of second embodiment dual coil vaporizer inhalation cartridge for high viscosity oil or resin.
Figure 16A:
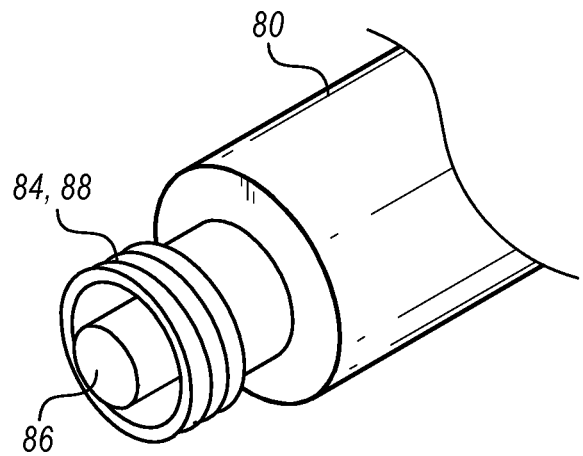
FIG. 16A is an enlarged view of the distal end of second embodiment dual coil vaporizer inhalation cartridge for high viscosity oil or resin.

| Term | Definition |
| --- | --- |
| 5 | Dual Coil Vaporizer Inhalation Cartridge for High Viscosity Oil or Resin |
| 10 | Mouthpiece |
| 12 | Vapor Tube |
| 14 | Tank Glass |
| 16 | Tank Chamber |
| 20 | Tank Heating Coil |
| 30 | Base |
| 32 | Vaporization Port |
| 34 | Wick Port |
| 36 | Vaporization Chamber |
| 38 | Air Vent |
| 40 | Wick |
| 42 | Electronics Chamber |
| 50 | Atomizer Heating Coil |
| 55 | Electrical Wiring |
| 60 | Voltage Regulator |
| 62 | Voltage Regulator Input Connection |
| 64 | Voltage Regulator Ground Connection |
| 66 | Voltage Regulator Output Connection |
| 70 | Single Pole Double Throw Switch (SPDTS) |
| 72 | SPDTS Input Connection |
| 74 | SPDTS First Output Connection |
| 76 | SPDTS Second Output Connection |
| 75 | Control Switch for Single Pole Double Throw Switch |
| 80 | Threaded Battery Connection |
| 82 | Female Thread |
| 84 | Male Thread |
| 86 | Center Electrical Contact |
| 87 | Insulation Cylinder |
| 90 | Battery Module |
| 95 | Battery Switch |
| 98 | Battery |
| 100 | High Viscosity Essential Oil or Resin |

DETAILED DESCRIPTION OF THE INVENTION

Dual coil vaporizer inhalation cartridge for high viscosity oil or resin 5 is a vaporizer or a cartridge used to vaporize substances for inhalation. Essential oils are the most common type of substance vaporized. Plant substances can be used, such as tobacco, cannabis, or other herbs, to create these essential oils. Oils can also be created with a combination of propylene glycol, glycerin, and drugs such as nicotine, tetrahydrocannabinol, or other drugs. When properly used, vaporizers operate at substantially cooler temperatures than the temperatures of combustion on a regular cigarette or pipe. Cooler temperatures result in significantly more efficient extraction of the desired ingredient, yielding less unwanted materials and contaminants in the vapor, as compared to smoke, which reduces irritation and the harmful effects of regular smoking and second hand smoke.

The greater the percentage of active ingredient in an inhalation oil, typically, the thicker or more viscous the inhalation oil is. Thus, potent oils are generally thicker than less potent oils. However, there is a maximum viscosity or thickness of inhalation oil that can be effectively processed through a vaporizer inhalation cartridge. A vaporizer inhalation cartridge typically uses a wick to absorb oil from the oil tank and transfer the oil to an atomizer heating coil where the oil is vaporized for inhalation. There is a maximum viscosity of the oil, above which, a wick is unable to transfer the oil through its capillary action. When this occurs, the vaporizer inhalation cartridge does not function. This invention, uses a tank heating coil inside of the oil tank that functions to heat and melt the oil/resin or otherwise lower its viscosity to allow the oil/resin to become more thin and runny so that the material may flow more easily through the wick and its capillary action to be successfully transferred to the atomizer heating coil for vaporization.

Dual coil vaporizer inhalation cartridge for high viscosity oil or resin 5 comprises: a mouthpiece 10, a vapor tube 12, a tank glass 14, a tank heating coil 20, a base 30, a wick 40, an atomizer heating coil 50, a voltage regulator 60, and a single pole double throw switch 70.

Mouthpiece 10 is a hollow rigid cylindrical shaped member with open ends. Mouthpiece 10 has a proximal end, a proximal end outer diameter, a distal end, a distal end outer diameter, an inner diameter, a length, and a longitudinal axis. The proximal end of mouthpiece 10 is inserted into the user's mouth in order to inhale the vapor and use the inhalation cartridge. The proximal end outer diameter of mouthpiece 10 is sized to comfortably fit inside a human's mouth. The distal end outer diameter of mouthpiece 10 is larger than that of the proximal end. The distal end of mouthpiece 10 is reversibly attachable to the distal end of vapor tube 12 and the distal end of tank glass 14. Reversible attachment may be accomplished by any known means such as a threaded connection, press fit, snap fit, tongue and groove rotation, or other. Tongue and groove rotation has a tongue or tab on one end that fits into an opening in a groove on the other end where the tongue is inserted and then rotated into the groove and away from the opening in the groove to attach the two members together. To remove, the tongue is rotated back to the opening in the groove and removed from the groove. In best mode, reversible attachment is accomplished by a threaded connection. Mouthpiece 10 may be made of any known material such as: metal, plastic, wood, glass, ceramic, or other.

Vapor tube 12 is a hollow rigid cylindrical shaped member with open ends. Vapor tube 12 has a proximal end, a distal end, an outer diameter, an inner diameter, a length, and a longitudinal axis. The inner diameter of vapor tube 12 is equal to that of mouthpiece 10. The proximal end of vapor tube 12 is reversibly attachable to the distal end of mouthpiece 10 so that the inner diameter of vapor tube 12 is flush with the inner diameter of mouthpiece 10. Reversible attachment may be accomplished by any known means such as a threaded connection, press fit, snap fit, tongue and groove rotation, or other. In best mode, reversible attachment is accomplished by a threaded connection. The longitudinal axis of vapor tube 12 is coincident with that of mouthpiece 10. The distal end of vapor tube 12 is rigidly attached to the proximal end of base 30. Rigid attachment may be accomplished by any known means such as weld, glue, epoxy, adhesive, bolts, screws, rivets, clips, or snaps. In best mode, rigid attachment is accomplished by a threaded connection. Vapor tube 12 may be made of any known material such as: metal, plastic, wood, glass, ceramic, or other. In best mode, vapor tube 12 is metal.

Tank glass 14 is a hollow rigid cylindrical shaped member with open ends. Tank glass 14 has a proximal end, a distal end, an outer diameter, an inner diameter, a length, and a longitudinal axis. The outer diameter of tank glass 14 is equal to that of the distal end of mouthpiece 10. The proximal end of tank glass 14 is reversibly attachable to the distal end of mouthpiece 10 so that the outer diameter of tank glass 14 is flush with the outer diameter of mouthpiece 10. Reversible attachment may be accomplished by any known means such as a threaded connection, press fit, snap fit, tongue and groove rotation, or other. In best mode, reversible attachment is accomplished by a threaded connection. The longitudinal axis of tank glass 14 is coincident with that of mouthpiece 10. The distal end of tank glass 14 is rigidly attached to the proximal end of base 30. Rigid attachment may be accomplished by any known means such as weld, glue, epoxy, adhesive, bolts, screws, rivets, clips, or snaps. In best mode, rigid attachment is accomplished by a threaded connection. Tank glass 14 may be made of any known material such as: metal, plastic, wood, glass, ceramic, or other. Tank glass 14 may be transparent, translucent, or opaque. In best mode, tank glass 14 is glass.

Dual coil vaporizer inhalation cartridge for high viscosity oil or resin 5 has a tank chamber 16. Tank chamber 16 is an internal cavity or chamber in between the vapor tube 12 and tank glass 14. Tank chamber 16 is a cavity, chamber, or tank that functions to retain or store the high viscosity essential oil or resin 100 that is used for vaporization. Tank chamber 16 is a cylindrical shaped or annular shaped cavity, chamber, or tank. Tank chamber 16 is defined by the distal end of mouthpiece 10, the outer diameter of vapor tube 12, the inner diameter of tank glass 14, and the proximal end of base 30. The upper boundary is the distal end of mouthpiece 10. The lower boundary is the proximal end of base 30. The inner boundary is outer diameter of vapor tube 12. The outer boundary is the inner diameter of tank glass 14. Thus, the latitudinal cross-section of tank chamber 16 is doughnut shaped.

Tank heating coil 20 is located inside tank chamber 16. Tank heating coil 20 is a heating element in the shape of a coil or helix. A heating element converts electrical energy into heat through the process of Joule heating where electric current passing through the heating element encounters resistance that results in the generation of heat. Any known type of heating element may be used for tank heating coil 20. Tank heating coil 20 functions to warm or heat the high viscosity essential oil or resin 100 prior to vaporization. Tank heating coil 20 heats up to conduct and radiate heat into the high viscosity essential oil or resin 100 stored inside the tank chamber 16. Tank heating coil 20 also conducts and radiates heat into the vapor tube 12, which in turn conducts and radiates heat into the high viscosity essential oil or resin 100 stored inside the tank chamber 16. The heating of high viscosity essential oil or resin 100 causes the high viscosity essential oil or resin 100 to melt or otherwise decrease its viscosity thereby thinning the high viscosity essential oil or resin 100 or making it more runny and thus more able to be captured or sucked in by wick 40. The heating of tank heating coil 20 requires delicate control. The high viscosity essential oil or resin 100 must not be heated up too much, or else the high viscosity essential oil or resin 100 vaporizes right there in the tank chamber 16. If this happens, the dual coil vaporizer inhalation cartridge for high viscosity oil or resin 5 does not function. On the other hand, the high viscosity essential oil or resin 100 must be heated enough to melt or otherwise decrease its viscosity enough for the high viscosity essential oil or resin 100 pass through the wick 40. There is a certain temperature window for each type of high viscosity essential oil or resin 100 to yield proper functioning of this invention. As discussed below, certain electronics are required to help control the heating of tank heating coil 20 and share a battery 98 with atomizer heating coil 50 from any standard battery module 90.

Tank heating coil 20 is attached to or fitted to the outside of vapor tube 12 so that tank heating coil 20 is coiled around the outside of vapor tube 12 and covers the outer diameter of vapor tube 12 as depicted. Tank heating coil 20 has an inner diameter, an outer diameter, a length, and a longitudinal axis. The inner diameter of tank heating coil 20 is slightly larger than the outer diameter of vapor tube 12 so that tank heating coil 20 forms a press fit, interference fit, or slip fit onto the outer diameter of vapor tube 12. The inner diameter of tank heating coil 20 is adjacent to and contiguous with the outer diameter of vapor tube 12 to make contact with the outer diameter of vapor tube 12. The length of tank heating coil 20 is equal to or slightly less than that of vapor tube 12 and tank glass 14. The longitudinal axis of Tank heating coil 20 is coincident with that of mouthpiece 10. Tank heating coil 20 has a proximal electrical contact and a distal electrical contact that are each an electrical contact or connector that may be any known type of electrical contact or connector. Proximal electrical contact and distal electrical contact that are each connected to electrical wiring 55. Electrical wiring 55 is electrical wiring that is typical electric wire used to pass electricity with a electrically conductive center surrounded by an insulated cover material. A battery 98 or power source is required to pass current through the tank heating coil 20 in order to operate it and cause it to heat up.

Base 30 is a rigid cylindrical member. Base 30 has a proximal end, a distal end, an outer diameter, a length, and a longitudinal axis. The outer diameter of base is equal to that of tank glass 14. The proximal end of base 30 is rigidly attached to the distal end of vapor tube 12 and the distal end of tank glass 14 so that the outer diameter of base 30 is flush with the outer diameter of tank glass 14. The longitudinal axis of base 30 is coincident with that of mouthpiece 10. Rigid attachment may be accomplished by any known means such as weld, glue, epoxy, adhesive, bolts, screws, rivets, clips, or snaps. In best mode, rigid attachment is accomplished by a threaded connection.

The proximal end of base 30 has five openings or ports: one vaporization port 32, two wick ports 34, and two wire ports. Vaporization port 32 is an opening or hole in the proximal end of base 30. Vaporization port 32 is a circular shaped opening or port between the distal end of vapor tube 12 and the vaporization port 32. Vaporization port 32 has an inner diameter and a center. The inner diameter of vaporization port 32 is equal to that of vapor tube 12. The center of vaporization port 32 is concentric with the longitudinal axis of vapor tube 12. The inner diameter of vaporization port 32 is flush with the inner diameter of vaporization tube. Vaporization port 32 has a proximal end and a distal end. The proximal end of vaporization port 32 is contiguous with the distal end of vapor tube 12 to allow access into the inner diameter of vapor tube 12. The distal end of vaporization port 32 is contiguous with a vaporization chamber 36 to allow access to the vaporization chamber 36. A wick port 34 is small opening or hole in the proximal end of base 30. Wick port 34 is a much smaller opening than vaporization port 32. Wick port 34 has a proximal end, a distal end, and a diameter. The diameter of wick port is slightly smaller than that of wick 40. The proximal end of wick port 34 is contiguous with tank chamber 16 to allow access into tank chamber 16. The distal end of wick port 34 is contiguous with a vaporization chamber 36 to allow access to the vaporization chamber 36. There are two wick ports in base 30, one wick port on each side of vaporization port 32 as depicted. A wire port is a small opening just large enough to pass electrical wiring 55 through where the electrical wiring 55 forms a press fit inside wire port to form a liquid tight and air tight connection therewith. There are two wire ports in base 30, one wire port on each side of vaporization port 32 as depicted.

Vaporization chamber 36 is an internal cavity or chamber inside of base 30 and within the interior of base 30. Vaporization chamber 36 has an access port or opening that is vaporization port 32. Vaporization chamber 36 is a hollow cylindrical shaped cavity with a bottom, a side, and a top. The bottom of vaporization chamber 36 is a closed barrier that is contiguous with the side of vaporization chamber 36, which is also a closed barrier. The top of vaporization chamber 36 is partially closed barrier with a circular shaped opening that is the vaporization port 32. The top of vaporization chamber 36 is contiguous with vaporization port 32 to yield an access port or opening in vaporization chamber 36.

There is a wick 40 inside of vaporization chamber 36. Wick 40 is a wick that is length of rope, cord, or fabric that absorbs and holds oil or liquid. Wicks work by capillary action, where small channels or tubes within the wick naturally suck or pull oil or liquid into them thereby conveying or transferring the oil or liquid from one end of the wick to the other. Wick 40 has a length, a diameter, a first end, a second end, and a middle section. The length of wick 40 is about 0.25 to 4 inches long. The first and second ends of wick 40 are located in tank chamber 16 as depicted. The middle section of wick 40 is located in vaporization chamber 36 as depicted. In this fashion wick 40 forms a U-shape. The first end of wick is passed through one wick port 34. The second end of wick 40 is passed through the second wick port 34. Wick 40 forms a press fit inside each wick port 34 that is a liquid tight fit that prevents liquid from passing between the outside of wick and the wick port 34. However, liquid may still pass through wick port 34 by passing through the center of the wick 40. When there is high viscosity essential oil or resin 100 in tank chamber 16, the first and second ends of wick 40 are in continuous contact with the high viscosity essential oil or resin 100.

There is an atomizer heating coil 50 inside of vaporization chamber 36. Atomizer heating coil 50 is a heating element in the shape of a coil or helix. Atomizer heating coil 50 has an inner diameter, an outer diameter, a length, and a longitudinal axis. Atomizer heating coil 50 has a first electrical contact and a second electrical contact that are each connected to electrical wiring 55. Atomizer heating coil 50 is attached to the bottom of vaporization chamber 36. The longitudinal axis of atomizer heating coil 50 is parallel with the bottom of vaporization chamber 36 and perpendicular to the longitudinal axis of mouthpiece 10. The first end of wick 40 is inserted through atomizer heating coil 50 and then passed through one wick port 34. The second end of wick 40 is passed through the other wick port 34 as depicted. Atomizer heating coil 50 is coiled around the middle section of wick 40 as depicted. Atomizer heating coil 50 functions to atomize or vaporize the high viscosity essential oil or resin 100 located and absorbed in the middle section of wick 40. When wick 40 is functioning properly, wick 40 naturally conveys high viscosity essential oil or resin 100 from its first and second ends to the middle section of wick 40. Thus, wick 40 continuously conveys high viscosity essential oil or resin 100 from the tank chamber 16 to the middle section of wick 40. When functioning properly the middle section of wick 40 is continuously saturated or moist with high viscosity essential oil or resin 100.

When atomizer heating coil 50 is turned on or powered on, atomizer heating coil 50 heats up to vaporize the high viscosity essential oil or resin 100 located in or absorbed in the middle section of wick 40. The vaporized high viscosity essential oil or resin 100 then fills the vaporization chamber 36 where it is then inhaled by the user who sucks it through the vaporization port 32, through the vapor tube 12, and into the user's mouth, which is attached to the proximal end of mouthpiece 10. As vapor is inhaled by the user, this creates a vacancy or void in the middle section of wick 40, which in turn causes more high viscosity essential oil or resin 100 to be soaked in from the first and second ends of wick 40 and passed to the middle section of wick 40, where it is vaporized and inhaled to sresint the process all over again. When functioning properly, the process continuously cycles or continuously passes or pulls high viscosity essential oil or resin 100 from the tank chamber 16 into the vaporization chamber 36, where it is vaporized in the middle of atomizer heating coil 50, and inhaled by the user through the vapor tube 12. This process continuously cycles until the atomizer coil 50 is turned off or powered off.

The heating of atomizer heating coil 50 requires delicate control. The high viscosity essential oil or resin 100 must be heated enough to vaporize the high viscosity essential oil or resin 100 inside the middle section of the wick 40 to allow for proper functioning of the dual coil vaporizer inhalation cartridge for high viscosity oil or resin 5. However, the high viscosity essential oil or resin 100 must not be heated so much as to ignite the high viscosity essential oil or resin 100 or cause it to combust. If this happens, the wick also ignites and burns which causes the dual coil vaporizer inhalation cartridge for high viscosity oil or resin 5 to fail. As discussed below, certain electronics are required to help control the heating of atomizer heating coil 50 and share a battery 98 with tank heating coil 20.

There is an electronics chamber 42 located distal to the vaporization chamber 36. Electronics chamber 42 is contiguous with the vaporization chamber 36. Electronics chamber 42 is separated from and isolated from vaporization chamber 36 by a barrier. Electronics chamber 42 is an internal cavity or chamber inside of base 30. Electronics chamber 42 houses or contains electronics such as: electrical wiring 55, a voltage regulator 60, and a single pole double throw switch 70. Electronics chamber 42 has a bottom, a side, and a top wherein each is a closed barrier in order to create a closed chamber. The bottom of electronics chamber 42 is a closed barrier that is contiguous with the side of electronics chamber 42, which is also a closed barrier. The side of electronics chamber 42 is a closed barrier that is contiguous with the top of electronics chamber 42, which is also a closed barrier, except for four wire ports.

There are four wire ports in the top of electronics chamber 42 for four lengths of electrical wiring 55. A wire port is a small opening just large enough to pass electrical wiring 55 through where the electrical wiring 55 forms a press fit inside wire port to form a liquid tight and air tight connection therewith. One electrical wire 55 is passed through each of the four wire ports to form a press fit within each wire port that is a liquid tight and air tight connection so that liquid or air cannot pass between the vaporization chamber 36 and the electronics chamber 42. The first electrical wire 55 passes through the first wire port in electronics chamber 42, into the vaporization chamber 36, then through the first wire port in the proximal end of base 30, and into the tank chamber 16, where is connected to the distal electrical contact on tank heating coil 20, as depicted, so that there is electrical continuity between these members. The other end of first electrical wire 55 is connected to the perimeter electrical contact 88, as depicted, so that there is electrical continuity between these members. The second electrical wire 55 passes through the second wire port in electronics chamber 42, into the vaporization chamber 36, where it is connected to the first electrical contact on atomizer heating coil 50, as depicted, so that there is electrical continuity between these members. The other end of second electrical wire 55 is connected to the perimeter electrical contact 88, as depicted, so that there is electrical continuity between these members. The third electrical wire 55 passes through the third wire port in electronics chamber 42, into the vaporization chamber 36, where it is connected to the second electrical contact on atomizer heating coil 50, as depicted, so that there is electrical continuity between these members. The other end of third electrical wire 55 is connected to the first output connection 74 of single pole double throw switch 70, as depicted, so that there is electrical continuity between these members. The fourth electrical wire 55 passes through the fourth wire port in electronics chamber 42, into the vaporization chamber 36, then through the second wire port in the proximal end of base 30, and into the tank chamber 16, where is connected to the proximal electrical contact on tank heating coil 20, as depicted, so that there is electrical continuity between these members. The other end of fourth electrical wire 55 is connected to the output connection 66 of voltage regulator 60, as depicted, so that there is electrical continuity between these members.

There are two wire ports in the bottom of electronics chamber 42 for two lengths of electrical wiring 55. One electrical wire 55 is passed through each of the two wire ports to form a press fit within each wire port that is a liquid tight and air tight connection so that liquid or air cannot pass between the electronics chamber 42 and threaded battery connection 80. The first electrical wire 55 passes through the first wire port in the bottom of electronics chamber 42, into the threaded battery connection 80, where is connected to the female thread 82 or male thread 84, as depicted, so that there is electrical continuity between these members. The other end of first electrical wire 55 passes into the vaporization chamber as depicted. The second electrical wire 55 passes through the second wire port in the bottom of electronics chamber 42, into the threaded battery connection 80, where it is connected to center electrical contact 86, as depicted, so that there is electrical continuity between these members. The other end of second electrical wire 55 is connected to the input connection 72 of single pole double throw switch 70, as depicted, so that there is electrical continuity between these members.

Voltage regulator 60 is a voltage regulator electronics component. A voltage regulator is a common electronics component. A voltage regulator is an integrated circuit or chip that automatically maintains a constant output voltage level, even with a varying or changing input voltage. A voltage regulator is typically attached to a circuit board along with other electronic components on the circuit board. Voltage regulator 60 functions to power and control tank heating coil 20. All electrical current used to heat and control tank heating coil 20 passes through voltage regulator 60. Any known type of voltage regulator electronics component may be used. Voltage regulator 60 has an input connection 62, a ground connection 64, and an output connection 66 that are each an electrical contact or connector. The input connection 62 of voltage regulator 60 can receive input voltage ranging from 1-20 volts direct current to produce an output voltage of 0.5-9 volts direct current, depending on how the voltage regulator is wired.

Figure 17:
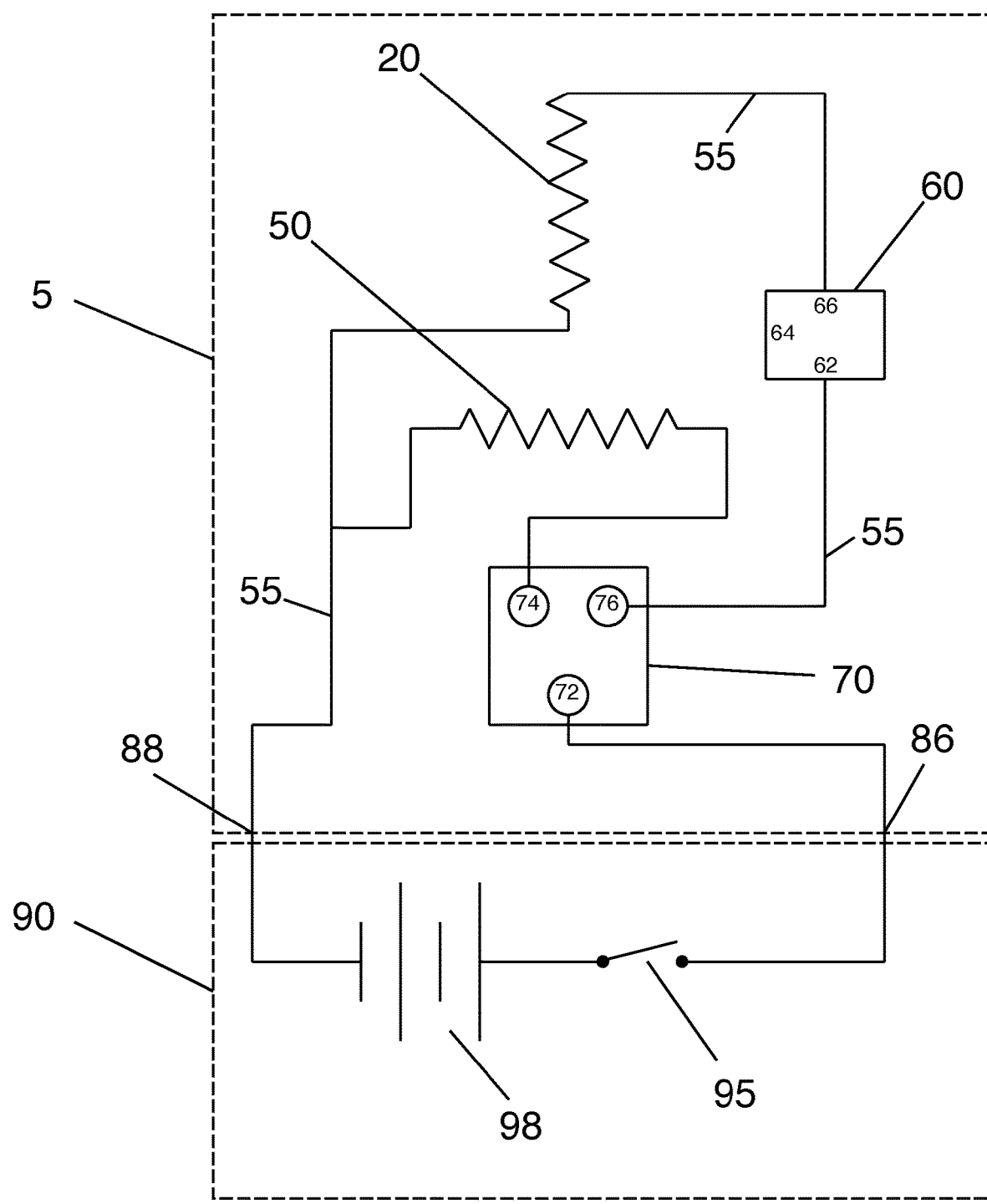
FIG. 17 is a circuit diagram depicting the electrical circuitry of a first mode of dual coil vaporizer inhalation cartridge for high viscosity oil or resin.
Figure 18:
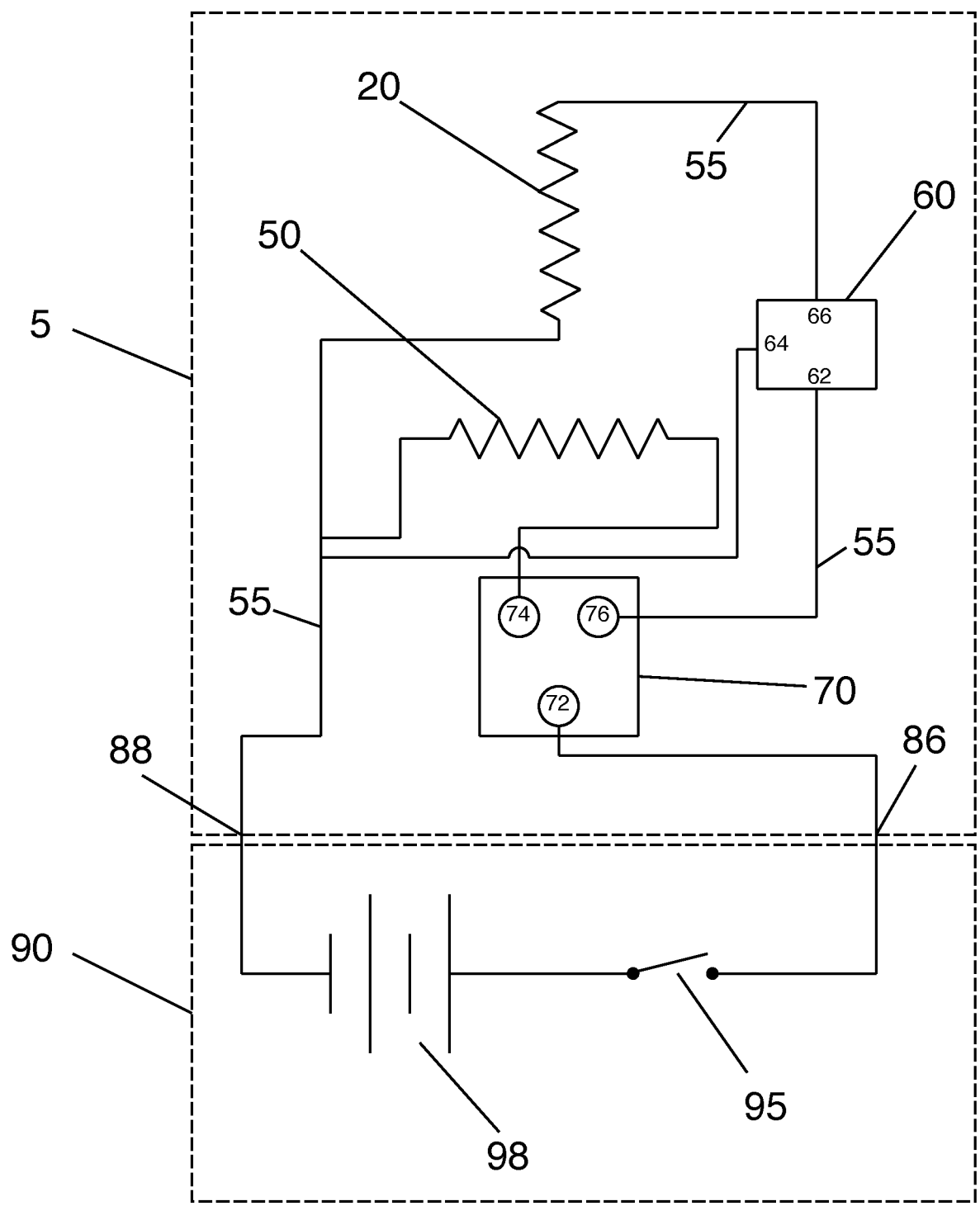
FIG. 18 is a circuit diagram depicting the electrical circuitry of a second mode of dual coil vaporizer inhalation cartridge for high viscosity oil or resin.
Figure 19:
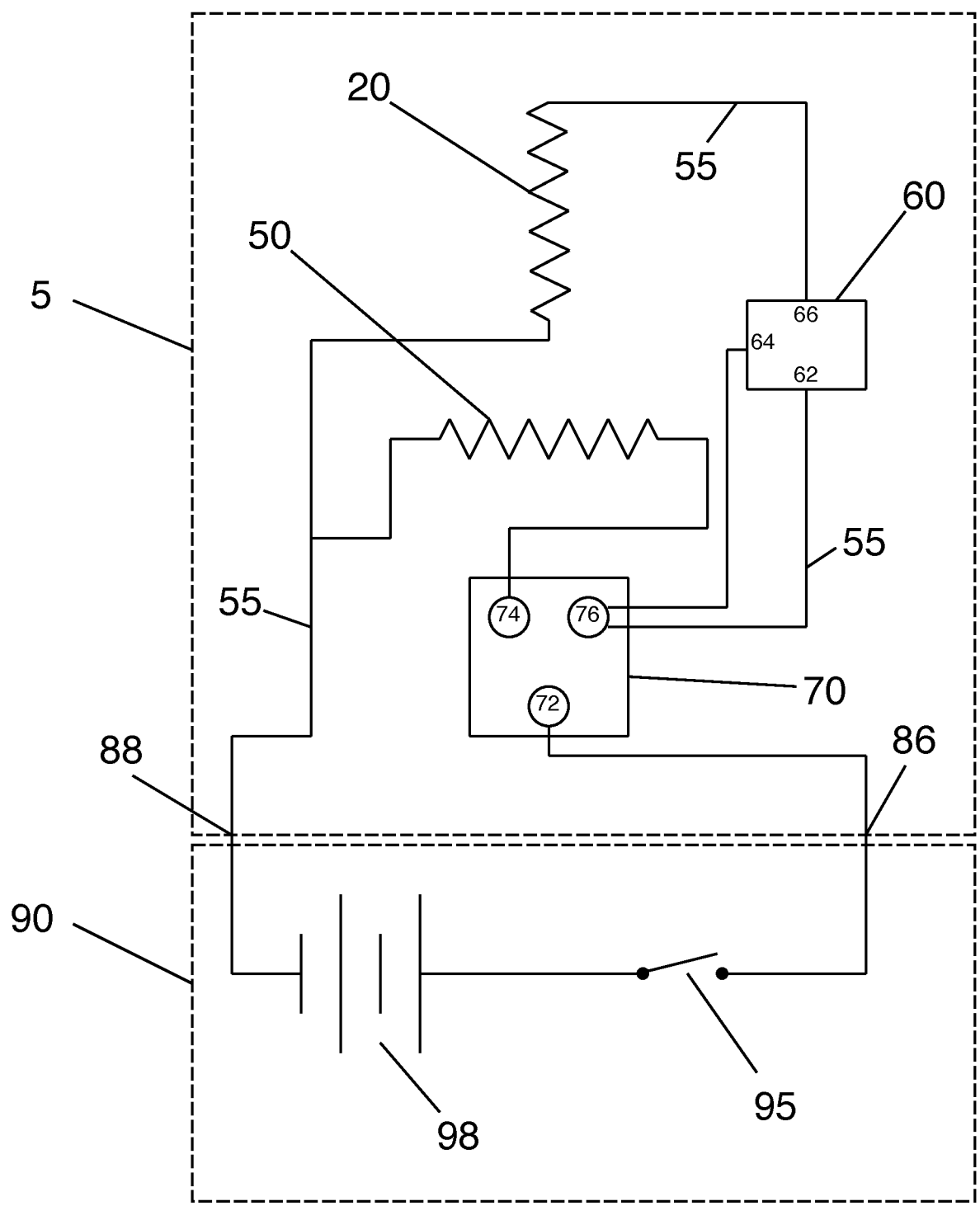
FIG. 19 is a circuit diagram depicting the electrical circuitry of a third mode of dual coil vaporizer inhalation cartridge for high viscosity oil or resin.

As discusses above, the control of tank heating coil 20 must be very delicate in order to meet the narrow temperature window required to melt or slightly melt the high viscosity essential oil or resin 100 without causing the high viscosity essential oil or resin 100 to vaporize in the tank chamber 16. In order to provide this delicate control, there are many different ways that voltage regulator 60 may be wired. In all modes, the output connection 66 of voltage regulator 60 is connected to the proximal electrical contact on tank heating coil 20 by electrical wiring 55 so that there is electrical continuity between these members. In one mode, the ground connection 64 of voltage regulator 60 is not used and is not connected to anything, as depicted in FIG. 17. This mode is designed to be used with high viscosity essential oil or resin 100 that falls in the lower viscosity range. In a second mode, the ground connection 64 of voltage regulator 60 is connected to the perimeter electrical contact 88 by electrical wiring 55 so that there is electrical continuity between these members, as depicted in FIG. 18. This mode is designed to be used with high viscosity essential oil or resin 100 that falls in the medium viscosity range. In a third mode, the ground connection 64 of voltage regulator 60 is connected to the second output connection 76 of single pole double throw switch 70 by electrical wiring 55 so that there is electrical continuity between these members, as depicted in FIG. 19. This mode is designed to be used with high viscosity essential oil or resin 100 that falls in the high viscosity range. Voltage regulator 60 may be wired by any known type of wiring scheme or schematic to provide any desired output voltage to tank heating coil 20.

Single pole double throw switch 70 is a single pole double throw switch. A single pole double throw switch is an electrical switch that has a single input that can connect to and switch between two outputs. A single pole double throw switch has one input terminal and two output terminals. Single pole double throw switch 70 has an input connection 72, a first output connection 74, second output connection 76, and a control switch 75. Control switch 75 for single pole double throw switch 70 is electrical switch. An electrical switch is a common electrical component used to make an electrical circuit, thereby diverting electrical current from one conductor to another. Control switch 75 has two positions. In the first position, there is electrical continuity between the input connection 72 and the first output connection 74. In the second position, there is electrical continuity between the input connection 72 and the second output connection 76. There are only two positions available on control switch 75. Control switch 75 is a selector switch on the outer diameter of base 30, which slides left and right. The left position corresponds to the first position. The right position corresponds to the second position. Typically, control switch 75 is integral with single pole double throw switch 70 and there is a small access hole in base 30 to provide access to the control switch 75. Electrical current is either directed to the first output connection 74 or to the second output connection 76. The input connection 72 of single pole double throw switch 70 is connected to center electrical contact 86 by electrical wiring 55 so that there is electrical continuity between these members. The first output connection 74 of single pole double throw switch 70 is connected to the second electrical connection of atomizer heating coil 50 by electrical wiring 55 so that there is electrical continuity between these members. The second output connection 76 of single pole double throw switch 70 is connected to the input connection 62 of voltage regulator 60 by electrical wiring 55 so that there is electrical continuity between these members.

There is a threaded battery connection 80 on the distal end of base 30 that is contiguous with electronics chamber 42. Threaded battery connection 80 has a closed barrier to the electronics chamber 42. Threaded battery connection 80 is reversibly attachable to a battery module 90. Threaded battery connection 80 may be accomplished by any known means of reversible attachment. Battery module 90 is not part of this invention. Threaded battery connection 80 is a means electromechanical reversible attachment to battery module 90. Threaded battery connection 80 provides a means of mechanical reversible attachment and a means of electronic reversible attachment. To attach dual coil vaporizer inhalation cartridge for high viscosity oil or resin 5 to battery module 90, threaded battery connection 80 is screwed or threaded onto battery module 90 and hand tightened. Threaded battery connection 80 may be female or male thread.

A dual coil vaporizer inhalation cartridge for high viscosity oil or resin 5 with female thread is depicted in FIGS. 1-8A. In this mode, threaded battery connection comprises: a female thread 82, a center electrical contact 86, and an insulation cylinder 87. Female thread 82 is a segment of female thread on the inside wall of the distal end of base 30. Female thread 82 is made of metal or other conductive material. Female thread 82 is reversibly attachable to and engages with a segment of male thread (not depicted) on battery module 90. Some battery modules 90 have male thread and some have female thread. Female thread 82 is also an electrical contact. When attached to the male thread on battery module 90, female thread 82 obviously makes physical contact with the male thread on battery module 90. This contact creates electrical continuity between these members. The male thread on battery module 90 has electrical continuity with the negative terminal on battery 98. Center electrical contact 86 is a rigid cylindrical member with a first end, a second end, an outer diameter, and a longitudinal axis. Center electrical contact 8 is made of metal or other conductive material. Center electrical contact 86 is an electrical pin connector. The longitudinal axis of center electrical contact 86 is coincident with that of base 30. The first end of center electrical contact 86 is rigidly attached to base 30. The first end of center electrical contact 86 is attached to a segment of electrical wiring 55 that is also attached to the input connection 72 of single pole double throw switch 70 so that there is electrical continuity between these members. When female thread 82 is attached to the male thread on battery module 90, the second end of center electrical contact 86 makes contact with a center pin (not depicted) on the battery module 90 to make electrical continuity therewith. The center pin on battery module 90 has electrical continuity with the positive terminal on battery 98. Thus, when attached to the male thread on battery module 90, female thread 82 has electrical continuity with the negative terminal on battery 98 and center electrical contact 86 has electrical continuity with the positive terminal on battery 98. Insulation cylinder 87 is a rigid cylindrical member made of non-conductive material. Insulation cylinder 87 has an inside diameter that slides over the outer diameter of center electrical contact 86. Insulation cylinder 87 has an outer diameter that slides into the inner diameter of threaded battery connection 80. Insulation cylinder 87 functions to separate female thread 82 and center electrical contact 86 and to prevent electrical arcing from occurring between the female thread 82 and the center electrical contact 86.

A dual coil vaporizer inhalation cartridge for high viscosity oil or resin 5 with male thread is depicted in FIGS. 9-16A. In this mode, threaded battery connection comprises: a male thread 84, a center electrical contact 86, and an insulation cylinder 87. Male thread 84 is a segment of male thread on the outside wall of the distal end of base 30. Male thread 84 is made of metal or other conductive material. Male thread 84 is reversibly attachable to and engages with a segment of female thread (not depicted) on battery module 90. Some battery modules 90 have male thread and some have female thread. Male thread 84 is also an electrical contact. When attached to the female thread on battery module 90, male thread 84 obviously makes physical contact with the female thread on battery module 90. This contact creates electrical continuity between these members. The female thread on battery module 90 has electrical continuity with the negative terminal on battery 98. Center electrical contact 86 is a rigid cylindrical member with a first end, a second end, an outer diameter, and a longitudinal axis. Center electrical contact 8 is made of metal or other conductive material. Center electrical contact 86 is an electrical pin connector. The longitudinal axis of center electrical contact 86 is coincident with that of base 30. The first end of center electrical contact 86 is rigidly attached to base 30. The first end of center electrical contact 86 is attached to a segment of electrical wiring 55 that is also attached to the input connection 72 of single pole double throw switch 70 so that there is electrical continuity between these members. When male thread 84 is attached to the female thread on battery module 90, the second end of center electrical contact 86 makes contact with a center pin (not depicted) on the battery module 90 to make electrical continuity therewith. The center pin on battery module 90 has electrical continuity with the positive terminal on battery 98. Thus, when attached to the female thread on battery module 90, male thread 84 has electrical continuity with the negative terminal on battery 98 and center electrical contact 86 has electrical continuity with the positive terminal on battery 98. Insulation cylinder 87 is a rigid cylindrical member made of non-conductive material. Insulation cylinder 87 has an inside diameter that slides over the outer diameter of center electrical contact 86. Insulation cylinder 87 has an outer diameter that slides into the inner diameter of threaded battery connection 80. Insulation cylinder 87 functions to separate male thread 84 and center electrical contact 86 and to prevent electrical arcing from occurring between the male thread 84 and the center electrical contact 86.

In order to load dual coil vaporizer inhalation cartridge for high viscosity oil or resin 5 with high viscosity essential oil or resin 100, mouthpiece 10 must be removed from vapor tube 12 and tank glass 14. Mouthpiece 10 is reversibly attachable to from vapor tube 12 and tank glass 14. Typically, mouthpiece 10 is unscrewed from vapor tube 12 and tank glass 14 to remove. This provides access to tank chamber 16. High viscosity essential oil or resin 100 may then be poured into tank chamber 16 or injected into tank chamber with a syringe. Then mouthpiece 10 is reinstalled onto vapor tube 12 and tank glass 14.

In order to use dual coil vaporizer inhalation cartridge for high viscosity oil or resin 5, dual coil vaporizer inhalation cartridge for high viscosity oil or resin 5 must be attached to a battery module 90. Battery module 90 has a battery switch 95 and a battery 98. Battery switch 95 controls battery 98. When battery switch 95 is engaged or depressed, the battery is engaged and turned on to have electrical continuity with the threaded battery connection 80 on dual coil vaporizer inhalation cartridge for high viscosity oil or resin 5. Dual coil vaporizer inhalation cartridge for high viscosity oil or resin 5 may be attached to any standard battery module.

In order to melt or reduce the viscosity of high viscosity essential oil or resin 100 stored in tank chamber 16, control switch 75 for single pole double throw switch 70 must be in the second position. In the figures, control switch 75 is depicted in the second position or right position. Then, the battery switch 95 is depressed, which sends power to the tank heating coil 20, thereby heating high viscosity essential oil or resin 100 in tank chamber 16. Battery switch 95 is held or depressed until the desired amount of high viscosity essential oil or resin 100 is melted or thinned, then the battery switch 95 is released or turned off.

In order to vaporize or inhale high viscosity essential oil or resin 100, control switch 75 for single pole double throw switch 70 must be in the first position. The user places his/her mouth on the distal end of mouthpiece 10. Then, the battery switch 95 is depressed, which sends power to the atomizer heating coil 50, thereby vaporizing the high viscosity essential oil or resin 100 in vaporization chamber 36, where it is inhaled through the vapor tube 12, and into the user's mouth. Battery switch 95 is held or depressed until the desired amount of vaporized high viscosity essential oil or resin 100 is inhaled, then the battery switch 95 is released or turned off.

What is claimed is:

1. A dual coil vaporizer inhalation cartridge for high viscosity oil or resin comprising: a mouthpiece; a vapor tube; a tank glass; a tank heating coil; a base; a wick; an atomizer heating coil; a voltage regulator; a single pole double throw switch, and electrical wiring, wherein, said mouthpiece is a hollow rigid cylindrical shaped member with a proximal end, a proximal end outer diameter, a distal end, a distal end outer diameter, an inner diameter, a length, and a longitudinal axis, wherein, said proximal end is open, and said distal end is open, said vapor tube is a hollow rigid cylindrical shaped member with a proximal end, a distal end, an outer diameter, an inner diameter, a length, and a longitudinal axis, wherein said proximal end is open, said distal end is open, said inner diameter of said vapor tube is equal to that of said mouthpiece, said proximal end of said vapor tube is reversibly attachable to said distal end of said mouthpiece so that said inner diameter of said vapor tube is flush with said inner diameter of said mouthpiece, said longitudinal axis of said vapor tube is coincident with that of said mouthpiece, and said distal end of said vapor tube is rigidly attached to a proximal end of a base, said tank glass is a hollow rigid cylindrical shaped member with a proximal end, a distal end, an outer diameter, an inner diameter, a length, and a longitudinal axis, wherein said proximal end is open, said distal end is open, said outer diameter of said tank glass is equal to that of said distal end of said mouthpiece, said proximal end of said tank glass is reversibly attachable to said distal end of said mouthpiece, said longitudinal axis of said tank glass is coincident with that of said mouthpiece, and said distal end of said tank glass is rigidly attached to said proximal end of said base, said tank heating coil is a heating element in the shape of a coil or helix with an inner diameter, an outer diameter, a length, a longitudinal axis, a proximal electrical contact, and a distal electrical contact, wherein, said tank heating coil is attached to or fitted to said outside of said vapor tube so that said tank heating coil is coiled around an outside of said vapor tube and covers said outer diameter of said vapor tube, said inner diameter of said tank heating coil is adjacent to and contiguous with said outer diameter of said vapor tube to make contact with said outer diameter of said vapor tube, said longitudinal axis of said tank heating coil is coincident with that of said mouthpiece, said proximal electrical contact is an electrical contact or connector, and said distal electrical contact is an electrical contact or connector that is connected to a length of said electrical wiring, said electrical wiring is electrical wiring that is typical electric wire used to pass electrical current with an electrically conductive center surrounded by an insulated cover material, said base is a rigid cylindrical member with a proximal end, a distal end, an outer diameter, an interior, a length, and a longitudinal axis, wherein, said proximal end of said base has a vaporization port that provides access to a vaporization chamber, said distal end of said base has a threaded battery connection that is reversibly attachable to a battery module, said outer diameter of said base is equal to that of said tank glass, said proximal end of said base is rigidly attached to said distal end of said vapor tube, said proximal end of said base is rigidly attached and said distal end of said tank glass so that said outer diameter of said base is flush with said outer diameter of said tank glass, said longitudinal axis of said base is coincident with that of said mouthpiece, said base houses or encloses the vaporization, the vaporization chamber is a chamber or internal cavity within said interior of said base that is adjacent to said vaporization port on said proximal end of said base, said base houses or encloses an electronics chamber that is a chamber or internal cavity within said interior of said base that is adjacent to said threaded battery connection on said distal end of said base, said wick is a wick or length of rope, cord, or fabric that absorbs and holds oil or liquid that is located in said vaporization chamber, said atomizer heating coil is a heating element in the shape of a coil or helix with an inner diameter, an outer diameter, a length, a longitudinal axis, a first electrical contact, and a second electrical contact, wherein, said atomizer heating coil is located in said vaporization chamber, said atomizer heating coil is coiled around said wick, said first electrical contact is an electrical contact or connector that is connected to a length of said electrical wiring, and said second electrical contact is an electrical contact or connector that is connected to a length of said electrical wiring, said voltage regulator is a voltage regulator electronics component that is an integrated circuit or chip with an input connection, a ground connection, and an output connection, wherein, said voltage regulator is located in said electronics chamber, said input connection is an electrical contact or connector, said ground connection is an electrical contact or connector, and said output connection is an electrical contact or connector that is connected to said proximal electrical contact on said tank heating coil by a length of said electrical wiring, said single pole double throw switch is an electrical switch with an input connection, a first output connection, second output connection, and a control switch, wherein, said single pole double throw switch is located in said electronics chamber, said input connection is an electrical contact or connector that is connected to a length of said electrical wiring, said first output connection is connected to said second electrical connection of said atomizer heating coil by a length of said electrical wiring, said second output connection is connected to said input connection of said voltage regulator by a length of said electrical wiring, said control switch is an electrical switch with a first position and a second position, wherein there is electrical continuity between said input connection and said first output connection when said control switch is in said first position and there is electrical continuity between said input connection and said second output connection when said control switch is in said second position.

2. A dual coil vaporizer inhalation cartridge for high viscosity oil or resin comprising: a mouthpiece; a vapor tube; a tank glass; a tank heating coil; a base; a wick; an atomizer heating coil; a voltage regulator; a single pole double throw switch, and electrical wiring, wherein, said mouthpiece is a hollow rigid cylindrical shaped member with a proximal end, a proximal end outer diameter, a distal end, a distal end outer diameter, an inner diameter, a length, and a longitudinal axis, wherein, said proximal end is open, and said distal end is open, said vapor tube is a hollow rigid cylindrical shaped member with a proximal end, a distal end, an outer diameter, an inner diameter, a length, and a longitudinal axis, wherein said proximal end is open, said distal end is open, said inner diameter of said vapor tube is equal to that of said mouthpiece, said proximal end of said vapor tube is reversibly attachable to said distal end of said mouthpiece so that said inner diameter of said vapor tube is flush with said inner diameter of said mouthpiece, said longitudinal axis of said vapor tube is coincident with that of said mouthpiece, and said distal end of said vapor tube is rigidly attached to a proximal end of a base, said tank glass is a hollow rigid cylindrical shaped member with a proximal end, a distal end, an outer diameter, an inner diameter, a length, and a longitudinal axis, wherein said proximal end is open, said distal end is open, said outer diameter of said tank glass is equal to that of said distal end of said mouthpiece, said proximal end of said tank glass is reversibly attachable to said distal end of said mouthpiece, said longitudinal axis of said tank glass is coincident with that of said mouthpiece, and said distal end of said tank glass is rigidly attached to said proximal end of said base, said tank heating coil is a heating element in the shape of a coil or helix with an inner diameter, an outer diameter, a length, a longitudinal axis, a proximal electrical contact, and a distal electrical contact, wherein, said tank heating coil is attached to or fitted to said outside of said vapor tube so that said tank heating coil is coiled around an outside of said vapor tube and covers said outer diameter of said vapor tube, said inner diameter of said tank heating coil is adjacent to and contiguous with said outer diameter of said vapor tube to make contact with said outer diameter of said vapor tube, said longitudinal axis of said tank heating coil is coincident with that of said mouthpiece, said proximal electrical contact is an electrical contact or connector, and said distal electrical contact is an electrical contact or connector that is connected to a length of said electrical wiring, said electrical wiring is electrical wiring that is typical electric wire used to pass electrical current with an electrically conductive center surrounded by an insulated cover material, said base is a rigid cylindrical member with a proximal end, a distal end, an outer diameter, an interior, a length, and a longitudinal axis, wherein, said proximal end of said base has a vaporization port that provides access to a vaporization chamber, said distal end of said base has a threaded battery connection that is reversibly attachable to a battery module, said outer diameter of said base is equal to that of said tank glass, said proximal end of said base is rigidly attached to said distal end of said vapor tube, said proximal end of said base is rigidly attached and said distal end of said tank glass so that said outer diameter of said base is flush with said outer diameter of said tank glass, said longitudinal axis of said base is coincident with that of said mouthpiece, said base houses or encloses the vaporization, the vaporization chamber is a chamber or internal cavity within said interior of said base that is adjacent to said vaporization port on said proximal end of said base, said base houses or encloses an electronics chamber that is a chamber or internal cavity within said interior of said base that is adjacent to said threaded battery connection on said distal end of said base, said wick is a wick or length of rope, cord, or fabric that absorbs and holds oil or liquid that is located in said vaporization chamber, said atomizer heating coil is a heating element in the shape of a coil or helix with an inner diameter, an outer diameter, a length, a longitudinal axis, a first electrical contact, and a second electrical contact, wherein, said atomizer heating coil is located in said vaporization chamber, said atomizer heating coil is coiled around said wick, said first electrical contact is an electrical contact or connector that is connected to a length of said electrical wiring, and said second electrical contact is an electrical contact or connector that is connected to a length of said electrical wiring, said voltage regulator is a voltage regulator electronics component that is an integrated circuit or chip with an input connection, a ground connection, and an output connection, wherein, said voltage regulator is located in said electronics chamber, said input connection is an electrical contact or connector, said ground connection is an electrical contact or connector that is connected to a length of said electrical wiring, and said output connection is an electrical contact or connector that is connected to said proximal electrical contact on said tank heating coil by a length of said electrical wiring, said single pole double throw switch is an electrical switch with an input connection, a first output connection, a second output connection, and a control switch, wherein, said single pole double throw switch is located in said electronics chamber, said input connection is an electrical contact or connector that is connected to a length of said electrical wiring, said first output connection is connected to said second electrical connection of said atomizer heating coil by a length of said electrical wiring, said second output connection is connected to said input connection of said voltage regulator by a length of said electrical wiring, said control switch is an electrical switch with a first position and a second position, wherein there is electrical continuity between said input connection and said first output connection when said control switch is in said first position and there is electrical continuity between said input connection and said second output connection when said control switch is in said second position.

3. A dual coil vaporizer inhalation cartridge for high viscosity oil or resin comprising: a mouthpiece; a vapor tube; a tank glass; a tank heating coil; a base; a wick; an atomizer heating coil; a voltage regulator; a single pole double throw switch, and electrical wiring, wherein, said mouthpiece is a hollow rigid cylindrical shaped member with a proximal end, a proximal end outer diameter, a distal end, a distal end outer diameter, an inner diameter, a length, and a longitudinal axis, wherein, said proximal end is open, and said distal end is open, said vapor tube is a hollow rigid cylindrical shaped member with a proximal end, a distal end, an outer diameter, an inner diameter, a length, and a longitudinal axis, wherein said proximal end is open, said distal end is open, said inner diameter of said vapor tube is equal to that of said mouthpiece, said proximal end of said vapor tube is reversibly attachable to said distal end of said mouthpiece so that said inner diameter of said vapor tube is flush with said inner diameter of said mouthpiece, said longitudinal axis of said vapor tube is coincident with that of said mouthpiece, and said distal end of said vapor tube is rigidly attached to a proximal end of a base, said tank glass is a hollow rigid cylindrical shaped member with a proximal end, a distal end, an outer diameter, an inner diameter, a length, and a longitudinal axis, wherein said proximal end is open, said distal end is open, said outer diameter of said tank glass is equal to that of said distal end of said mouthpiece, said proximal end of said tank glass is reversibly attachable to said distal end of said mouthpiece, said longitudinal axis of said tank glass is coincident with that of said mouthpiece, and said distal end of said tank glass is rigidly attached to said proximal end of said base, said tank heating coil is a heating element in the shape of a coil or helix with an inner diameter, an outer diameter, a length, a longitudinal axis, a proximal electrical contact, and a distal electrical contact, wherein, said tank heating coil is attached to or fitted to said outside of said vapor tube so that said tank heating coil is coiled around an outside of said vapor tube and covers said outer diameter of said vapor tube, said inner diameter of said tank heating coil is adjacent to and contiguous with said outer diameter of said vapor tube to make contact with said outer diameter of said vapor tube, said longitudinal axis of said tank heating coil is coincident with that of said mouthpiece, said proximal electrical contact is an electrical contact or connector, and said distal electrical contact is an electrical contact or connector that is connected to a length of said electrical wiring, said electrical wiring is electrical wiring that is typical electric wire used to pass electrical current with an electrically conductive center surrounded by an insulated cover material, said base is a rigid cylindrical member with a proximal end, a distal end, an outer diameter, an interior, a length, and a longitudinal axis, wherein, said proximal end of said base has a vaporization port that provides access to a vaporization chamber, said distal end of said base has a threaded battery connection that is reversibly attachable to a battery module, said outer diameter of said base is equal to that of said tank glass, said proximal end of said base is rigidly attached to said distal end of said vapor tube, said proximal end of said base is rigidly attached and said distal end of said tank glass so that said outer diameter of said base is flush with said outer diameter of said tank glass, said longitudinal axis of said base is coincident with that of said mouthpiece, said base houses or encloses the vaporization, the vaporization chamber is a chamber or internal cavity within said interior of said base that is adjacent to said vaporization port on said proximal end of said base, said base houses or encloses an electronics chamber that is a chamber or internal cavity within said interior of said base that is adjacent to said threaded battery connection on said distal end of said base, said wick is a wick or length of rope, cord, or fabric that absorbs and holds oil or liquid that is located in said vaporization chamber, said atomizer heating coil is a heating element in the shape of a coil or helix with an inner diameter, an outer diameter, a length, a longitudinal axis, a first electrical contact, and a second electrical contact, wherein, said atomizer heating coil is located in said vaporization chamber, said atomizer heating coil is coiled around said wick, said first electrical contact is an electrical contact or connector that is connected to a length of said electrical wiring, and said second electrical contact is an electrical contact or connector that is connected to a length of said electrical wiring, said voltage regulator is a voltage regulator electronics component that is an integrated circuit or chip with an input connection, a ground connection, and an output connection, wherein, said voltage regulator is located in said electronics chamber, said input connection is an electrical contact or connector, said ground connection is an electrical contact or connector that is connected to said second output connection of said single pole double throw switch by a length of said electrical wiring, and said output connection is an electrical contact or connector that is connected to said proximal electrical contact on said tank heating coil by a length of said electrical wiring, said single pole double throw switch is an electrical switch with an input connection, a first output connection, a second output connection, and a control switch, wherein, said single pole double throw switch is located in said electronics chamber, said input connection is an electrical contact or connector that is connected to a length of said electrical wiring, said first output connection is connected to said second electrical connection of said atomizer heating coil by a length of said electrical wiring, said second output connection is connected to said input connection of said voltage regulator by a length of said electrical wiring, said control switch is an electrical switch with a first position and a second position, wherein there is electrical continuity between said input connection and said first output connection when said control switch is in said first position and there is electrical continuity between said input connection and said second output connection when said control switch is in said second position.

* * * * *